US006537230B1

(12) United States Patent
Pfeiffer et al.

(10) Patent No.: US 6,537,230 B1
(45) Date of Patent: Mar. 25, 2003

(54) APPARATUS, COMPUTER SYSTEM AND COMPUTER PROGRAM FOR DETERMINING A CARDIO-VASCULAR PARAMETER OF A PATIENT

(75) Inventors: Ulrich J. Pfeiffer, Munich (DE); Thorsten Burger, Munich (DE)

(73) Assignee: Pulsion Medical Systems AG, Munich (DE)

( * ) Notice: Subject to any disclaimer, the term of this patent is extended or adjusted under 35 U.S.C. 154(b) by 0 days.

(21) Appl. No.: 09/869,354

(22) PCT Filed: Oct. 27, 2000

(86) PCT No.: PCT/EP00/10590

§ 371 (c)(1),
(2), (4) Date: Oct. 1, 2001

(87) PCT Pub. No.: WO01/30237

PCT Pub. Date: May 3, 2001

Related U.S. Application Data (60) Provisional application No. 60/161,931, filed on Oct. 28, 1999.

(51) Int. Cl.[7] .................................................. A61B 5/02
(52) U.S. Cl. ........................ 600/526; 600/505; 600/549
(58) Field of Search ................................. 600/505, 549, 600/526

(56) References Cited

U.S. PATENT DOCUMENTS 4,230,126 A * 10/1980 Elings ........................ 600/484
4,417,588 A * 11/1983 Houghton et al. .......... 600/526
4,542,748 A * 9/1985 Roy ............................ 600/526
6,394,961 B1 * 5/2002 Pfeiffer et al. .............. 600/526

* cited by examiner

Primary Examiner—Robert L. Nasser
Assistant Examiner—Patricia Mallari
(74) Attorney, Agent, or Firm—Nixon Peabody LLP; Donald R. Studebaker (57) ABSTRACT

A computer system (104) is connected to an injection means (107) to inject at a first place (101) a bolus warmer or colder than patient's blood. The travelling temperature deviation thus introduced to the patient's vascular system (103) passes the pulmonary circulation (111), where an extravascular thermovolume (112) may be present. When the temperature deviation reaches the second place (102), where blood temperature is measured by a sensor device (117) connected to the computer system (104), it is recorded as Thermodilution Curve (15), from which the computer system (104) determines an extravascular thermovolume estimate. Depending on that result the computer system (104) calculates a new amount of bolus to be injected by the injection means (107). The higher the extravascular thermovolume estimate, the higher the new amount of bolus. The new travelling temperature deviation thus introduced to patient's vascular system (103) eventually reaches the second place (102), where it is recorded as an improved Thermodilution Curve (17) from which cardio-vascular parameters of improved accuracy are derived by the computer system (104).

21 Claims, 8 Drawing Sheets

APPARATUS, COMPUTER SYSTEM AND COMPUTER PROGRAM FOR DETERMINING A CARDIO-VASCULAR PARAMETER OF A PATIENT

FIELD OF THE INVENTION

The present invention relates to an apparatus, a computer system and a computer program for determining a cardio-vascular parameter of a patient by thermodilution measurements.

BACKGROUND OF THE INVENTION

Figure 1:
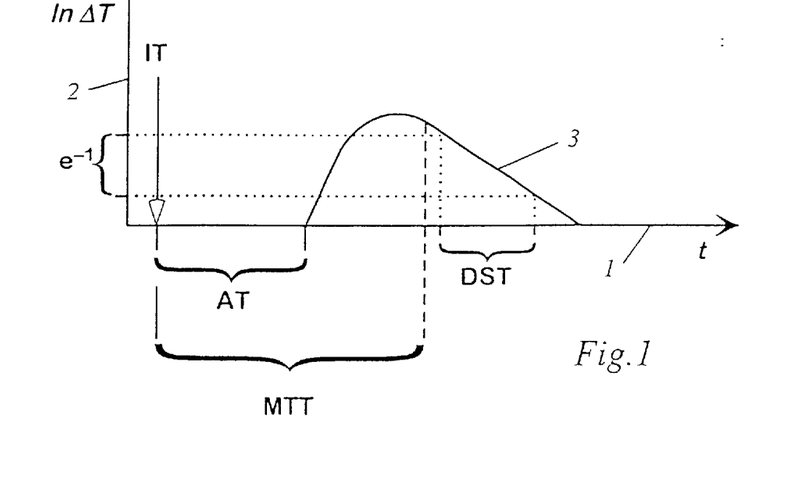
FIG. 1 shows a schematic example of a Thermodilution Curve in a diagram with the blood temperature difference as a function of time, wherein the abscissa is linear and the ordinate is logarithmic.

The current state of the art in implementing transpulmonary thermodilution measurement are apparatus for injecting a bolus of thermal indicator into a patient's vena cava superior, and measuring the temperature response at a place of the patient's systemic circulation, e.g. patient's arteria femoralis to determine the Thermodilution Curve, i.e. the temperature response as a function of time. From the thermodilution curve, a schematic example of which is illustrated in FIG. 1, wherein the abscissa (time axis) 1 is linear and the ordinate (temperature difference axis) 2 is logarithmic, various cardio-vascular parameters can be derived by using computersystems running computer programs, which implement parameter calculations as disclosed in WO 93/21823, the contents of which are included herein by citation, and as set forth briefly below.

The Cardiac Output CO can be determined by algorithms based on the Stewart-Hamilton-equation:

$$CO = \frac{V_L(T_B - T_L)K_1K_2}{\int \Delta T_B(t)dt}$$

where $T_B$ is the initial blood temperature, $T_L$ is the temperature of the liquid bolus, which is used as thermal indicator, $V_L$ is the thermal indicator volume, $K_1$ and $K_2$ are constants to consider the specific measurement setup, and $\Delta T_B(t)$ is the blood temperature as a function of time with respect to the baseline blood temperature $T_B$. Thermal indicator can either be colder or warmer with respect to blood temperature. To obtain cardiac output, the area under the thermodilution curve has to be integrated.

Other parameters that can be derived from the thermodilution curve 3 as schematically illustrated in FIG. 1 include the Exponential Decay or Downslope Time DST, i.e. the time the blood temperature difference $\Delta T_B(t)$ takes to drop by the factor $e^{-1}$, the Appearence Time AT, i.e. the time span between bolus injection IT and first appearence of a noticable temperature difference $\Delta T_B(t)$ and the Mean Transit Time MTT.

The Intrathoracic Thermovolume ITTV and the Intrathoracic blood volume ITBV can be determined as follows:

ITTV=CO·MTT

ITBV=a'·GEDV+b' wherein a' and b' are species-specific constants and GEDV is the Global End-Diastolic Volume, which can be determined as follows:

GEDV=CO·(MTT−DST)

An extravascular thermovolume estimate can be determined as the difference between Intrathoracic Thermovolume ITTV and the Intrathoric blood volume ITBV

ETV=ITTV−ITBV

Extravascular thermovolume correlates, if there is no significant perfusion deffect in the lungs (e.g. pulmonary embolism), closely to the degree of Extravascular Lung Water. However, the clinical value of that measurement has not been shown explicitly yet.

Figure 2:
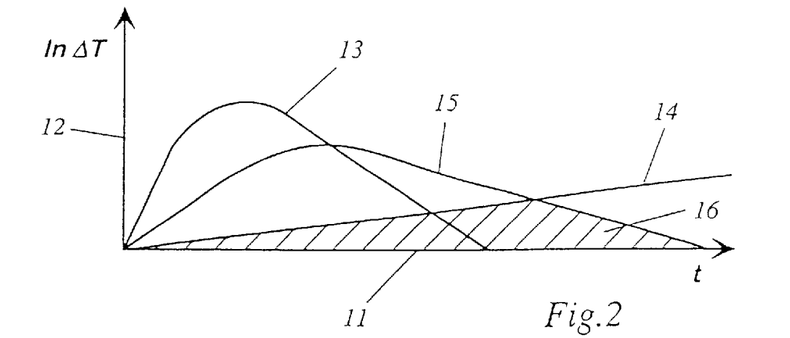
FIG. 2 shows two schematic examples of Thermodilution Curves, once without a considerable extravascular thermovolume and once with a considerable extravascular thermovolume, in a diagram with the respective blood temperature response, wherein the abscissa (time axis) is linear and the ordinate is logarithmic, and a baseline drift has occurred.

A diagram similar to FIG. 1 is shown in FIG. 2 illustrating the problem of a baseline drift of the blood temperature. Again, the abscissa (time axis) 11 is linear and the ordinate (temperature difference axis) 12 is logarithmic. The baseline drift is indicated by baseline 14, the drift being shown excessive for the purpose of illustration. The schematically shown transpulmonary Thermodilution Curves 13, 15 with the same, constant Cardiac Output result from different boundary conditions. The first Thermodilution Curve 13 has been determined without the presence of a substantial extravascular thermovolume, whereas the second Thermodilution Curve 15 is broader and exhibits a less pronounced blood temperature peak due to the presence of a substantial extravascular thermovolume. The hatched area 16 illustrates the error of the area under the blood temperature curves 13, 15 and thus the error of the Cardiac Output determined from each curve due to the baseline drift. It is obvious, that determining Cardiac Output from the second Thermodilution Curve 15 will suffer from a significantly larger error due to baseline drift than determining Cardiac Output from the first Thermodilution Curve 13.

The object of the present invention is therefore to reduce the error in Cardiac Output determination due to a baseline drift, when a substantial extravascular thermovolume is present, and thus improve accuracy and reliability of determining cardio-vascular parameters by thermodilution measurements.

SUMMARY OF THE INVENTION

In order to accomplish the above mentioned object, the present invention provides an apparatus for determining a cardio-vascular parameter of a patient by thermodilution measurements comprising temperature influencing means for provoking an initial local temperature change in the proximity of a first place of a patient's vascular system thus introducing a travelling temperature deviation to patient's blood stream, further comprising a temperature sensor device for measuring the local temperature of patient's blood at a second place of patient's vascular system downstream of the first place, further comprising a computer connected to the temperature sensor device for recording the patient's local blood temperature measured at the second place as a function of time to determine a thermodilution curve, determining an extravascular thermovolume estimate from the thermodilution curve, determining a new initial local temperature change depending on the thermovolume estimate, controlling the temperature influencing means to provoke the new initial local temperature change in the proximity of the first place, determining an improved thermodilution curve, and determining the cardio-vascular parameters from the improved thermodilution curve.

In order to accomplish the above mentioned object, the present invention also provides a computer system comprising first connection means to connect the computer system to temperature influencing means and second connection means to connect the computer system to a temperature sensor device, and accessing means to acces executable instructions to cause the computer system to control temperature influencing means connected to the computer system to provoke an initial local temperature change in the proximity of a first place of a patient's vascular system, thus introducing a travelling temperature deviation to patient's blood stream, to record the patient's local blood temperature measured by a temperature sensor device at a second place of patient's vascular system downstream of the first place as a function of time to determine a thermodilution curve, to determine an extravascular thermovolume estimate from the thermodilution curve, to determine a new initial local temperature change depending on the thermovolume estimate, to control the temperature influencing means to provoke the new initial local temperature change in the proximity of the first place, to determine an improved thermodilution curve, and to determine the cardio-vascular parameters from the improved thermodilution curve.

In order to accomplish the above mentioned object, the present invention also provides a computer program for determining the cardio-vascular parameters of a patient by thermodilution measurements comprising instructions executable by a computer system to cause the computer system to control temperature influencing means connected to the computer system to provoke an initial local temperature change in the proximity of a first place of a patient's vascular system, thus introducing a travelling temperature deviation to patient's blood stream, to record the patient's local blood temperature measured by a temperature sensor device at a second place of patient's vascular system downstream of the first place as a function of time to determine a thermodilution curve, to determine an extravascular thermovolume estimate from the thermodilution curve, to determine a new initial local temperature change depending on the thermovolume estimate, to control the temperature influencing means to provoke the new initial local temperature change in the proximity of the first place, to determine an improved thermodilution curve, and to determine the cardio-vascular parameters from the improved thermodilution curve.

In order to accomplish the above mentioned object, the present invention also provides a storage medium having physically stored thereon a computer program for determining the cardio-vascular parameters of a patient by thermodilution measurements comprising instructions executable by a computer system to cause the computer system to control temperature influencing means connected to the computer system to provoke an initial local temperature change in the proximity of a first place of a patient's vascular system, thus introducing a travelling temperature deviation to patient's blood stream, to record the patient's local blood temperature measured by a temperature sensor device at a second place of patient's vascular system downstream of the first place as a function of time to determine a thermodilution curve, to determine an extravascular thermovolume estimate from the thermodilution curve, to determine a new initial local temperature change depending on the thermovolume estimate, to control the temperature influencing means to provoke the new initial local temperature change in the proximity of the first place, to determine an improved thermodilution curve, and to determine the cardio-vascular parameters from the improved thermodilution curve.

In a preferred embodiment of the present invention, the temperature influencing means is an injection means for injecting a liquid having a temperature different from the temperature of patient's blood, provoking the initial local temperature change is achieved by the injection means injecting at the first place a first amount of liquid into the vascular system, the liquid having a first temperature different from the temperature of patient's blood, and provoking the new temperature difference is achieved by the injection means injecting at the first place a second amount of liquid into the vascular system, the liquid having a second temperature different from the temperature of patient's blood.

In another preferred embodiment of the present invention, the second temperature is different from the first temperature.

In another preferred embodiment of the present invention, the second amount is different from the first amount.

In another preferred embodiment of the present invention, the cardio-vascular parameter is determined by transpulmonary thermodilution and the extravascular thermovolume estimate correlates to an estimate of Extravascular Lung Water. Extravascular thermovolume correlates, if there is no significant perfusion deffect in the lungs (e.g. pulmonary embolism), closely to the degree of Extravascular Lung Water. However, the clinical value of that measurement has not been shown explicitly yet.

In another preferred embodiment of the present invention, the extravascular thermovolume estimate is determined from a cardiac output estimate derived from the thermodilution curve, a downslope of the thermodilution curve, and a mean transit time estimate derived from the thermodilution curve indicating an estimate of the time required by the temperature deviation to travel from the first place to the second place.

In another preferred embodiment of the present invention, the cardio-vascular parameter to be determined is the cardiac output.

The accompanying drawings serve for a better understanding of the above and other features of the present invention.

BRIEF DESCRIPTION OF THE DRAWINGS

FIGS. 6 a–e together form a flowchart (with connecting nodes A, B, C, D) illustrating an embodiment of a computer program according to the present invention, to be run on the computer system of FIG. 5.

DETAILED DESCRIPTION

Figure 3:
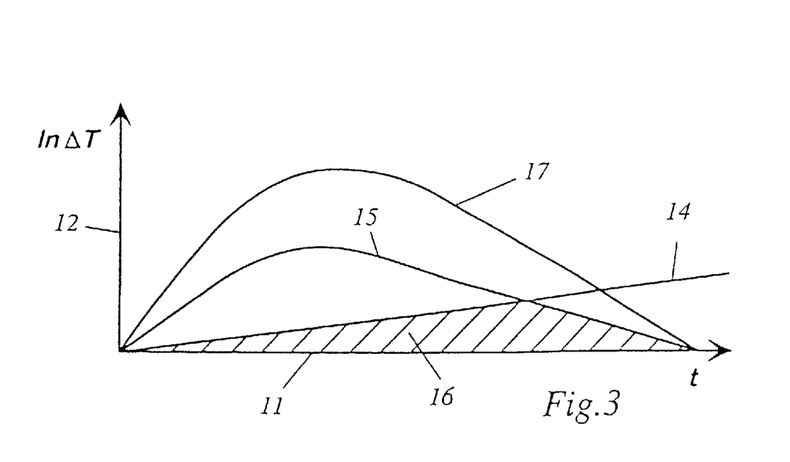
FIG. 3 shows two schematic examples of Thermodilution Curves with a considerable extravascular thermovolume, once with a smaller and once with a larger amount of bolus injected, in a diagram with the respective blood temperature response, wherein the abscissa (time axis) is linear and the ordinate is logarithmic, and a baseline drift has occurred.

The problem of potentially inaccurate Cardiac Output determination in case of a baseline drift shown in FIG. 2 and described above can be reduced by increasing the amount of bolus to be injected as schematically shown in FIG. 3 and as implemented by the present invention. As in FIG. 2, in FIG. 3 the abscissa (time axis) 11 is linear and the ordinate (temperature difference axis) 12 is logarithmic. Again the baseline drift is indicated by baseline 14, the drift being shown excessive for the purpose of illustration. The schematically shown transpulmonary Thermodilution Curves 15, 17 with the same, constant Cardiac Output result from different amounts of bolus injected. The flatter Thermodilution Curve 15 has been determined with a smaller thermal indicator volume, whereas the amount of bolus injected has been increased for determining improved Thermodilution Curve 17. The hatched area 16 illustrates the error of the area under the blood temperature curve 15 and thus the error of the Cardiac Output determined from that curve due to the baseline drift. Determining Cardiac Output from the improved Thermodilution Curve 17 will result in increased accuracy, since the area below the baseline 14 and the improved Thermodilution Curve 17 is fairly small compared to overall area below Thermodilution Curve 17.

Figure 4:
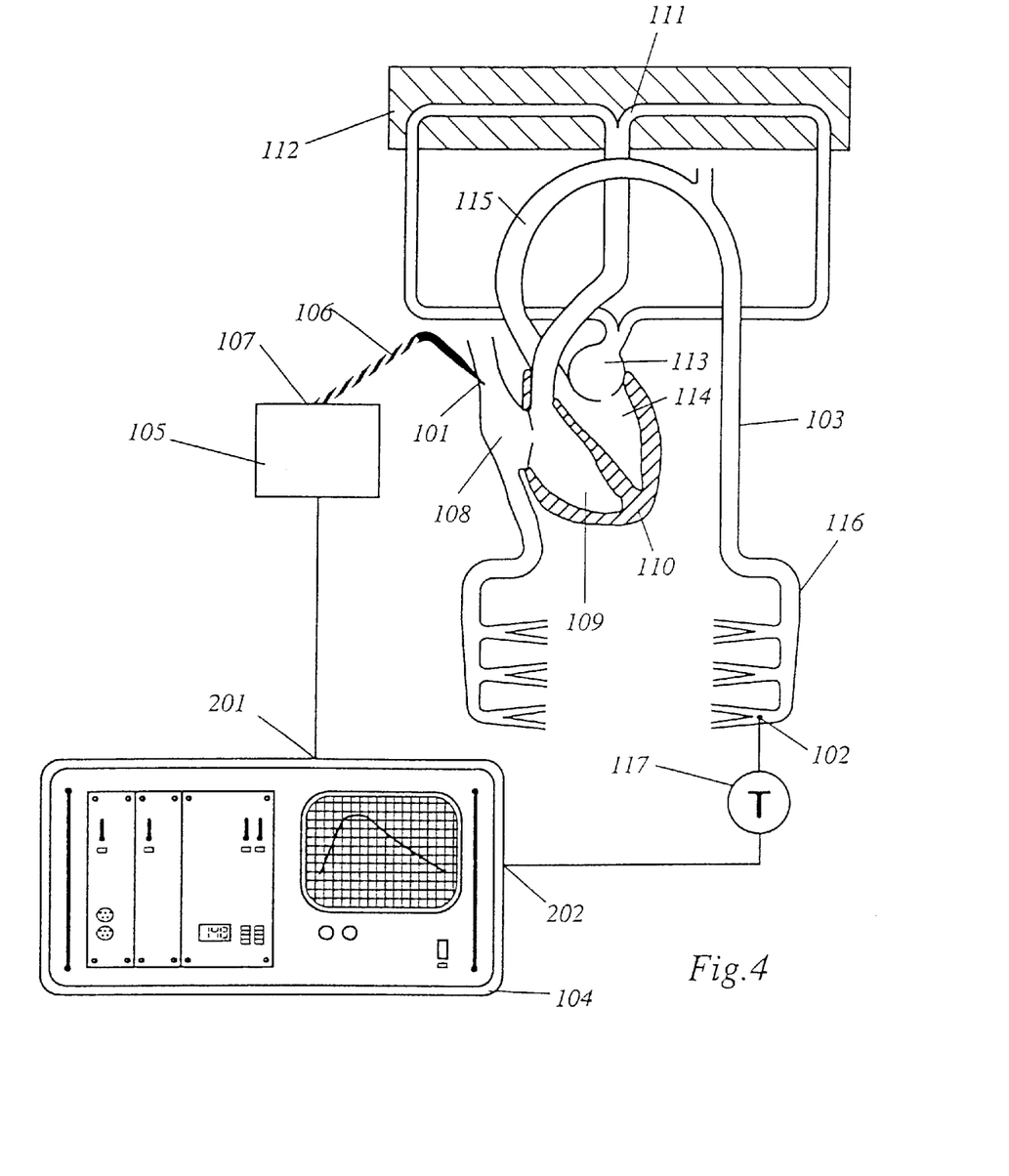
FIG. 4 shows a schematic sketch of both a patient's vascular system and a preferred embodiment of an apparatus according to the present invention.
Figure 5:
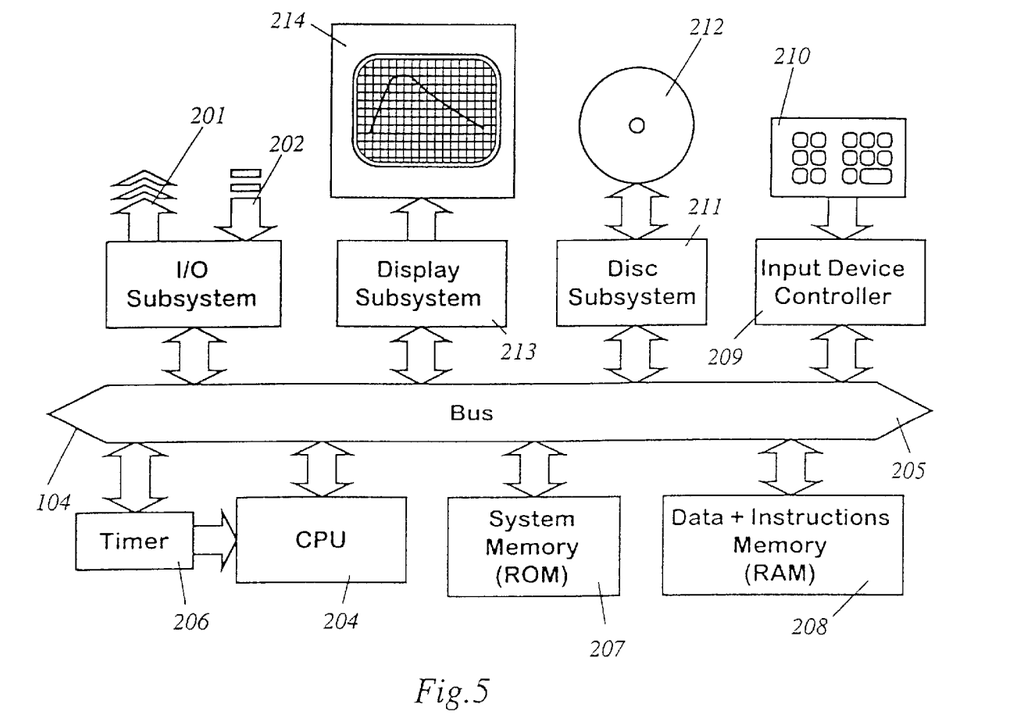
FIG. 5 shows a block diagram illustrating the general hardware structure of an embodiment of a computer system according to the present invention being part of the apparatus sketched in FIG. 4.

FIG. 4 illustrates the main components necessary to implement an embodiment of an apparatus according to the invention and schematically shows the first and second places 101, 102 of a patient's vascular system 103, where the apparatus interacts with the patient's vascular system 103. A computer system 104, the general hardware structure of which is schematically illustrated in FIG. 5, is connected via port A 201 with a medical dosage device 105 serving together with a catheter 106 as an injection means 107 to inject at the first place 101, e.g. into patient's vena cava superior, a bolus, e.g. 10 ml, or, as a guideline, 0.15 ml/kg patient's body mass. The bolus serving as a thermal indicator liquid is substantially warmer or colder than patient's blood temperature As a result, travelling temperature deviation is introduced to the patient's vascular system 103, where it continuously changes according to boundary conditions. The travelling temperature deviation passes right atrium and right ventricle 109 of patient's heart 110 to enter the pulmonary circulation 111, where an extravascular thermovolume 112 may be present in the proximity of the patient's vessels. The travelling temperature deviation passes the left atrium 113 and the left ventricle 114 of patient's heart to enter through the aorta 115 the systemic circulation 116. When the travelling temperature deviation reaches the second place 102, e.g. patient's arteria femoralis, where the patient's blood temperature is continuously measured by a sensor device 117, which is connected to the computer system 104 via port B 202, the travelling temperature deviation is recorded by the computer system 104 as Thermodilution Curve 15, i.e. temperature measured at the second place 102 as function of time. From this Thermodilution Curve 15 the computer system 104 determines an extravascular thermovolume estimate according to the relations explained above. Extravascular thermovolume correlates, if there is no significant perfusion deffect in the lungs (e.g. pulmonary embolism), closely to the degree of Extravascular Lung Water. However, the clinical value of that measurement has not been shown explicitly yet.

Depending on this extravascular thermovolume estimate the computer system 104 calculates a new amount of bolus to be injected by the injection means 107. The higher the extravascular thermovolume estimate, the higher will be the new amount of bolus to be injected. Incjecting the new amount of bolus introduces in the proximity of the first place 101 a new travelling temperature deviation, which eventually reaches the second place 102, where it is recorded by the computer system 104 as an improved Thermodilution Curve 17. From this improved Thermodilution Curve 17 cardio-vascular parameters, e.g. Cardiac Output, of improved accuracy are derived in the above-described manner and displayed by the computer system 104.

FIG. 5 illustrates the general hardware structure of an embodiment of a computer system 104 according to the invention, suitable to be part of the apparatus shown in FIG. 4 and to run the program illustrated by the flow chart in FIGS. 6a–e. Via ports A and B 201, 202 which belong to an input/output subsystem 203, the computer system 104 is connectable to injection means 107 and sensor device 117, respectively. The input/output subsystem 203 is controlled by a central processing unit (CPU) 204, which communicates via a data and adress bus 205 with the other components of the computer system 104, which include a timer 206 providing timer clock signals to the CPU 204, a system memory (ROM) 207, in which the system software is permanently stored, a data and instructions memory (RAM) 208, where both executable instructions and various data including temperature readings for Thermodilution Curves can be stored, an input device controller 209 controlling an input device 210, such as a keypad, a touch screen or the like, for manually entering system parameters, operation settings and the like, a disc subsystem 211 to read data or program instructions from a storage medium 212, such as a hard disc, floppy disc, compact disc or the like, and to store data to the storage medium 212, and a display subsystem 213 controlling a display 214 to display relevant information, such as a Thermodilution Curve or cardio-vascular parameters determined by the computer system 104.

Figure 6A:
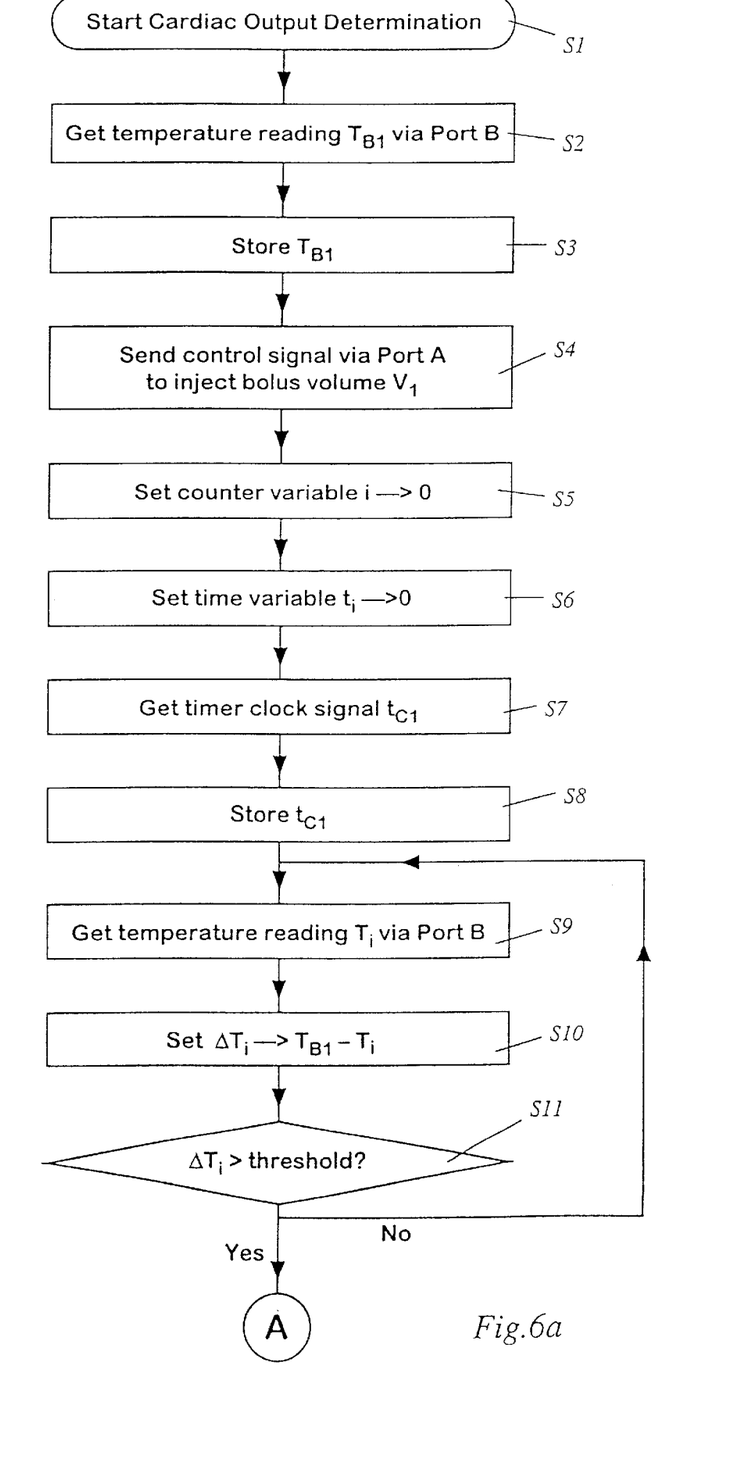

FIG. 6a is the first part of a flow chart extending over FIGS. 6a to 6e, illustrating the step sequence of an embodiment of a programm to determine Cardiac Output according to the invention, which can be executed by a computer system 104 as schematically shown in FIG. 5. After the program has been loaded from the storage medium 212 into the RAM 208 and started (Step S1) it causes the computer system 104 to retrieve via port B 202 from sensor device 117 an initial blood temperature reading $T_{B1}$ measured at the second place 102 of patient's vascular system 103, e.g. at the arteria femoralis (Step S2). $T_{B1}$ is stored into the RAM 208 (Step S3) and a control signal sent via port A 201 to injection means 107 to inject a bolus volume $V_1$, e.g. 10 ml or 0,15 ml per kg patient's body mass, at first place 101 of patient's vascular system 103, e.g. into the vena cava superior (Step S4). Counter variable i is set to 0 (Step S5), time variable $t_i$ is set to 0 (Step S6) and the current timer clock signal $t_{C1}$, which is used as a reference time and represents Injection Time IT, being supplied to the CPU 204 by timer 206 (Step S7) is stored into the RAM 208 (Step S8). A blood temperature reading $T_i$ measured at the second place 102 of patient's vascular system 103 is retrieved via port B 202 from sensor device 117 (Step S9). Variable $\Delta T_i$ is set to $T^{B1}-T_i$, i.e. the difference between current temperature reading and initial temperature reading (Step S10), and compared to a predetermined first threshold (Step S11) in order to determine, whether a temperature response is already noticeable. If $\Delta T_i$ is below threshold, the program returns to Step S9. If $\Delta T_i$ is above threshold, the program continues with step S12 in FIG. 6b.

Figure 6B:
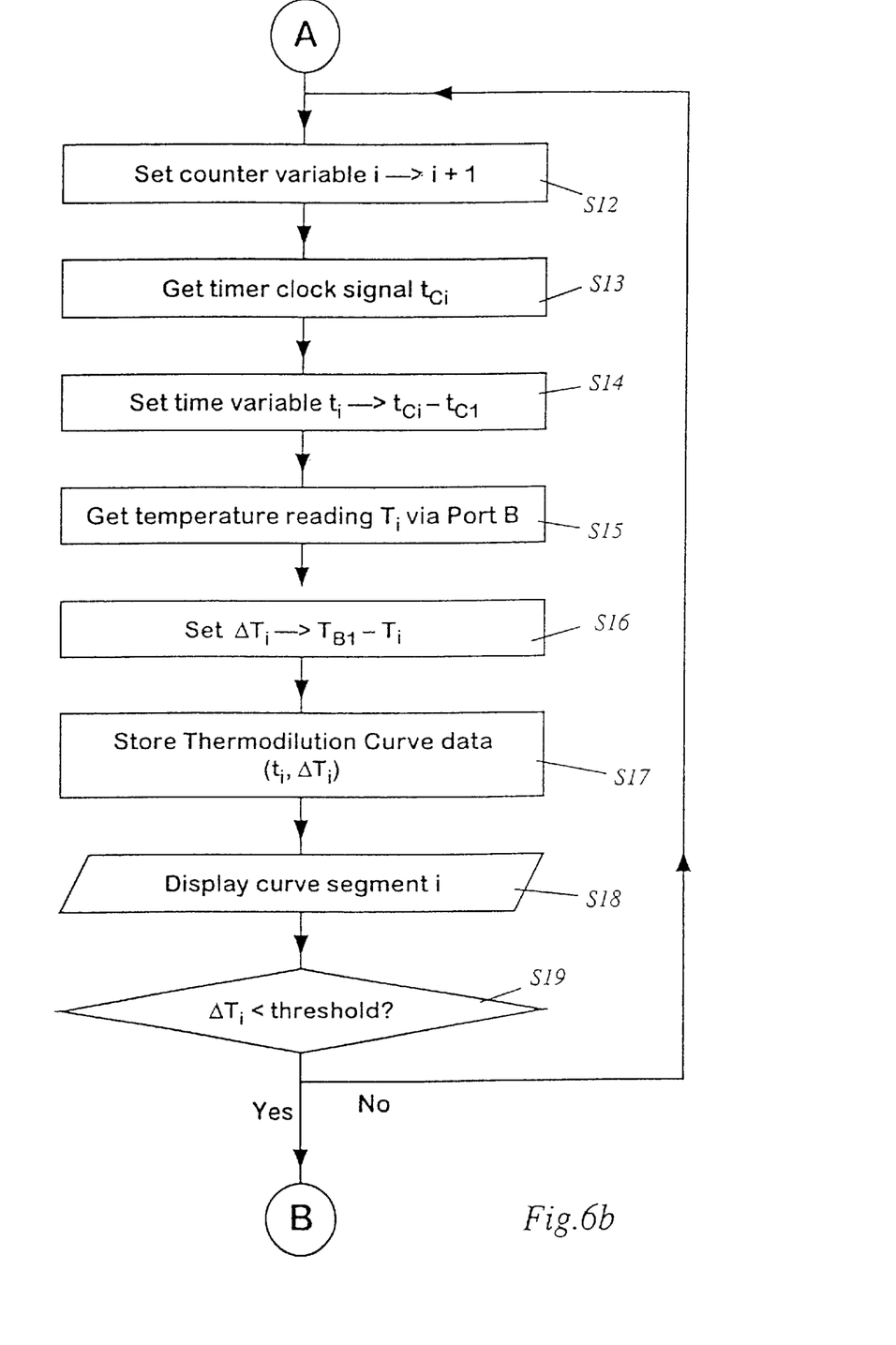

FIG. 6b is the second part of the flow chart extending over FIGS. 6a to 6e. Counter variable i is increased by one (Step S12) and time variable $t_i$ is set to the difference between the current timer clock signal $t_{Ci}$ being supplied to the CPU 204 by timer 206 (Step S13) and the stored time $t_{C1}$ (Step S14). A new blood temperature reading $T_i$ measured at the second place 102 of patient's vascular system 103 is retrieved via port B 202 from sensor device 117 (Step S15). Variable $\Delta T_i$ is set to $T_{B1}-T_i$, i.e. the difference between current temperature reading and initial temperature reading (Step S16), and both $\Delta T_i$ and $t_i$, representing a data point of the Thermodilution Curve, are stored into the RAM (Step S17). The current Thermodilution curve segment is displayed on the display 214 by the display subsystem 213 (Step S18). $\Delta T_i$ is compared to a predetermined second threshold (Step S19) in order to determine, whether the travelling temperature deviation has already completely passed the second place 102 of patient's vascular system 103. If $\Delta T_i$ is above threshold, the program returns to Step S12. If $\Delta T_1$ is below threshold, the program continues with step S20 in FIG. 6c.

Figure 6C:
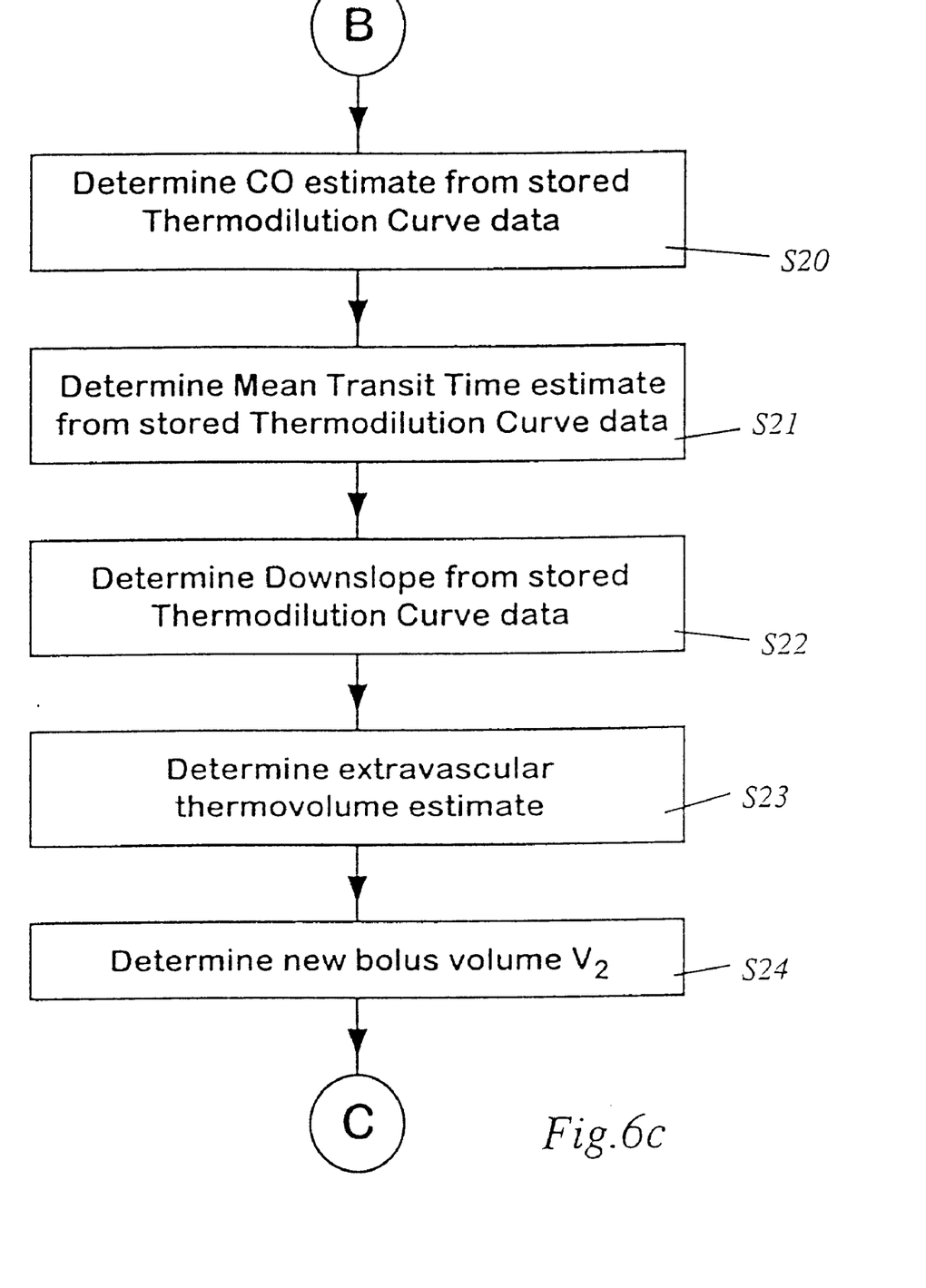

FIG. 6c is the third part of the flow chart extending over FIGS. 6a to 6e. In the manner described above, a cardiac output estimate is determined from stored Thermodilution Curve data (Step S20) as well as a Mean Transit Time estimate (Step S21) and the exponential decay time DST of the Thermodilution Curve (Step S22). These parameters are used by the program to determine an extravascular thermovolume estimate in the manner described above (Step S24). Extravascular thermovolume correlates, if there is no significant perfusion deffect in the lungs (e.g. pulmonary embolism), closely to the degree of Extravascular Lung Water. However, the clinical value of that measurement has not been shown explicitly yet. Depending on the extravascular thermovolume estimate, a new bolus volume $V_2$ to be injected at first place 101 of patient's vascular system 103 is determined, for example by comparing the extravascular thermovolume estimate with reference values stored in a table in the RAM 208, the ROM 207 or the storage medium 212. The higher the extravascular thermovolume estimate, the higher is $V_2$. Then the program procedes to Step S25 in FIG. 6d.

Figure 6D:
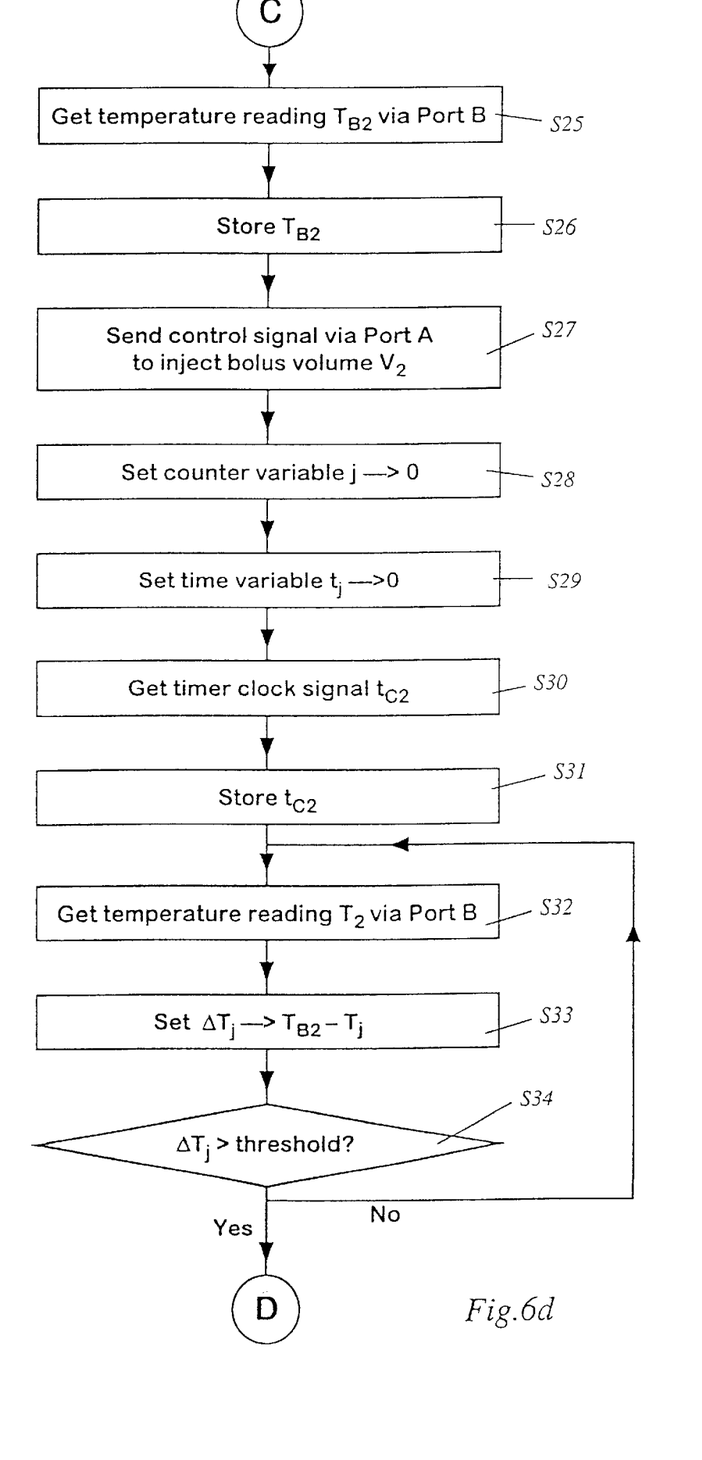

FIG. 6d is the fourth part of the flow chart extending over FIGS. 6a to 6e. A new initial blood temperature reading $T_{B2}$ measured at the second place 102 of patient's vascular system 103 is retrieved via port B 202 from sensor device 117 (Step S25). $T_{B2}$ is stored into the RAM 208 (Step S26) and a control signal sent via port A 201 to injection means 107 to inject the new bolus volume $V_2$ at first place 101 of patient's vascular system 103 (Step S27). Counter variable j is set to 0 (Step 528), time variable $t_j$ is set to 0 (Step S29) and the current timer clock signal $t_{C2}$, which is used as a reference time and represents new Injection Time IT, being supplied to the CPU 204 by timer 206 (Step S30) is stored into the RAM 208 (Step S31). A blood temperature reading $T_j$ measured at the second place 102 of patient's vascular system 103 is retrieved via port B 202 from sensor device 117 (Step S32). Variable $\Delta T_j$ is set to $T_{B2}-T_j$, i.e. the difference between current temperature reading and new initial temperature reading (Step S33), and compared to a predetermined first threshold (Step S34) in order to determine, whether a temperature response is already noticeable. If $\Delta T_j$ is below threshold, the program returns to Step S32. If $\Delta T_i'$ is above threshold, the program continues with step S35 in FIG. 6e.

Figure 6E:
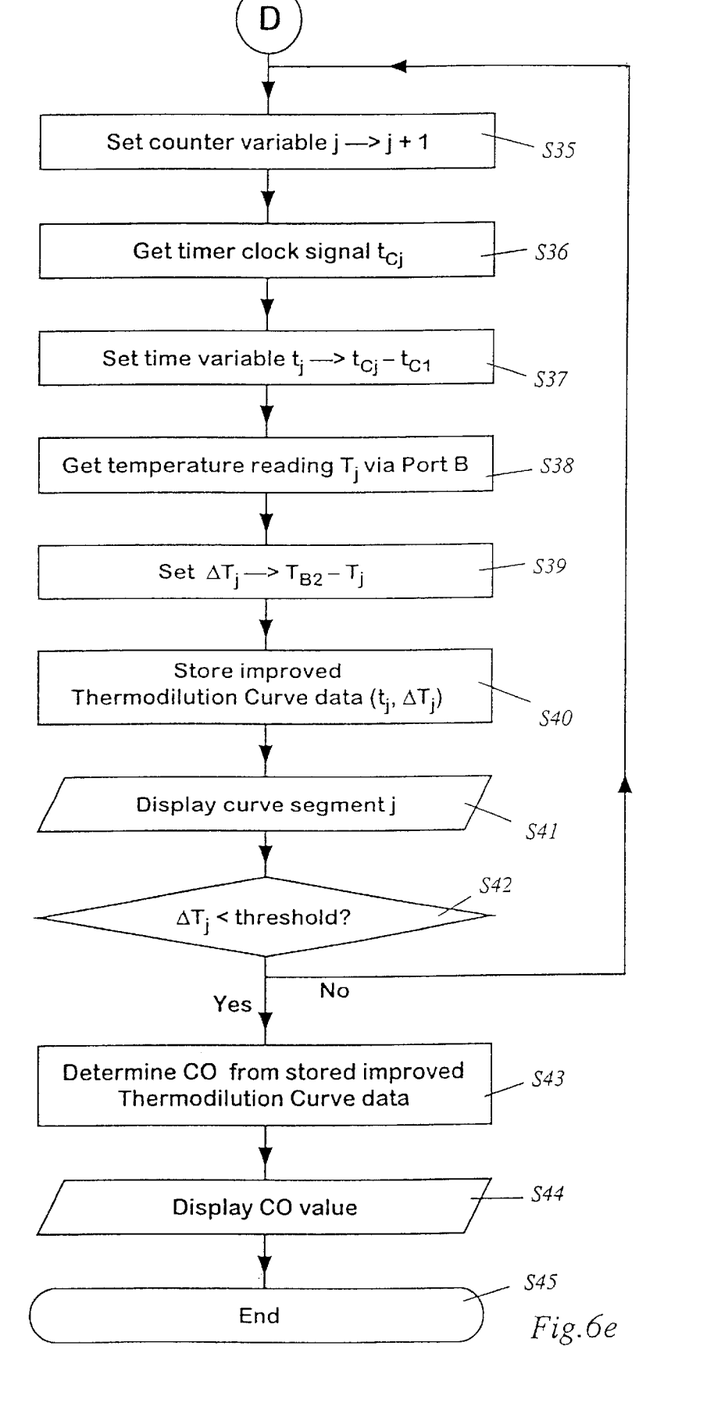

FIG. 6e is the fifth part of the flow chart extending over FIGS. 6a to 6e. Counter variable j is increased by one (Step S35) and time variable $t_j$ is set to the difference between the current timer clock signal $t_{C2}$ being supplied to the CPU 204 by timer 206 (Step S36) and the stored time $t_{C2}$ (Step S37). A new blood temperature reading $T_j$ measured at the second place 102 of patient's vascular system 103 is retrieved via port B 202 from sensor device 117 (Step S38). Variable $\Delta T_j$ is set to $T_{B2}-T_j$, i.e. the difference between current temperature reading and initial temperature reading (Step S39), and both $\Delta T_j$ and $t_j$, representing a data point of an improved Thermodilution Curve, are stored into the RAM (Step S40). The current improved Thermodilution curve segment is displayed on the display 214 by the display subsystem 213 (Step S41). $\Delta T_j$ is compared to a predetermined second threshold (Step S42) in order to determine, whether the travelling temperature deviation has already completely passed the second place 102 of patient's system 103. If $\Delta T_j$ is above threshold, the program returns to Step S35. If $\Delta T_i'$ is below threshold, Cardiac Output is determined in the manner described above (Step S43) and displayed on the display 214 by the display subsystem 213 (Step S44).

What is claimed is:

1. Apparatus for determining a cardio-vascular parameter of a patient by thermodilution measurements comprising:
   a) temperature influencing means (107) for provoking an initial local temperature change in the proximity of a first place (101) of a patient's vascular system (103), thus introducing a travelling temperature deviation to patient's blood stream,
   b) a temperature sensor device (117) for measuring the local temperature of patient's blood at a second place (102) of patient's vascular system (103) downstream of said first place (101)
   c) a computer system (104) connected to said temperature sensor device (117) for recording said patient's local blood temperature measured at said second place (102) as a function of time to determine a thermodilution curve (15),
   determining an extravascular thermovolume (112) estimate from said thermodilution curve (15),
   determining a new initial local temperature change depending on said thermovolume (112) estimate,
   controlling said temperature influencing means (107) to provoke said new initial local temperature change in the proximity of said first place (101),
   determining an improved thermodilution curve (17), and determining said cardio-vascular parameter from said improved thermodilution curve (17).

2. Apparatus as claimed in claim 1, wherein said temperature influencing means (107) is an injection means (107) for injecting a liquid having a temperature different from the temperature of patient's blood,
   provoking said initial local temperature change is achieved by said injection means (107) injecting at said first place (101) a first amount of liquid into said vascular system (103), said liquid having a first temperature different from the temperature of patient's blood,
   and provoking said new temperature difference is achieved by said injection means (107) injecting at said first place (101) a second amount of liquid into said vascular system (103), said liquid having a second temperature different from the temperature of patient's blood.

3. Apparatus as claimed in claim 2 wherein said second temperature is different from said first temperature.

4. Apparatus as claimed in any one of claims 2 or 3, wherein said second amount is different from said first amount.

5. Apparatus as claimed in claim 1 wherein said cardiovascular parameter is determined by transpulmonary thermodilution and said extravascular thermovolume (112) estimate correlates to an estimate of Extravascular Lung Water.

6. Apparatus as claimed in claim 1 wherein said extravascular thermovolume (112) estimate is determined from a cardiac output estimate derived from said thermodilution curve (15), a downslope of said thermodilution curve (15), and a mean transit time estimate derived from said thermodilution curve (15) indicating an estimate of the time required by said temperature deviation to travel from said first place (101) to said second place (102).

7. Apparatus as claimed in claim 1 wherein said cardiovascular parameter is the cardiac output.

8. Computer system (104) comprising first connection means to connect said computer system (104) to temperature influencing means (107) and second connection means to connect said computer system (104) to a temperature sensor device (117), and accessing means to acces executable instructions to cause said computer system (104)

a) to control temperature influencing means (107) connected to said computer system (104) to provoke an initial local temperature change in the proximity of a first place (101) of a patient's vascular system (103), thus introducing a travelling temperature deviation to patient's blood stream, b) to record said patient's local blood temperature measured by a temperature sensor device (117) at a second place (102) of patient's vascular system (103) downstream of said first place (101) as a function of time to determine a thermodilution curve (15), c) to determine an extravascular thermovolume (112) estimate from said thermodilution curve (15), d) to determine a new initial local temperature change depending on said thermovolume (112) estimate, e) to control said temperature influencing means (107) to provoke said new initial local temperature change in the proximity of said first place (101), f) to determine an improved thermodilution curve (17), and g) to determine said cardio-vascular parameter from said improved thermodilution curve (17).

9. Computer system (104) as claimed in claim 8, wherein said temperature influencing means (107) is an injection means (107) for injecting a liquid having a temperature different from the temperature of patient's blood, provoking said initial local temperature change is achieved by said injection means (107) injecting at said first place (101) a first amount of liquid into said vascular system (103), said liquid having a first temperature different from the temperature of patient's blood, and provoking said new temperature difference is achieved by said injection means (107) injecting at said first place (101) a second amount of liquid into said vascular system (103), said liquid having a second temperature different from the temperature of patient's blood.

10. Computer system (104) as claimed in claim 9, wherein said second temperature is different from said first temperature.

11. Computer system (104) as claimed in any of claims 9 or 10, wherein said second amount is different from said first amount.

12. Computer system (104) as claimed in claim 8 wherein said cardio-vascular parameter is determined by transpulmonary thermodilution and said extravascular thermovolume (112) estimate correlates to an estimate of Extravascular Lung Water.

13. Computer system (104) as claimed in claim 8 wherein said extravascular thermovolume (112) estimate is determined from a cardiac output estimate derived from said thermodilution curve (15), a downslope of said thermodilution curve (15), and a mean transit time estimate derived from said thermodilution curve (15) indicating an estimate of the time required by said temperature deviation to travel from said first place (101) to said second place (102).

14. Computer system (104) as claimed in claim 8 wherein said cardio-vascular parameter is the cardiac output.

15. Computer program for determining a cardio-vascular parameter of a patient by thermodilution measurements comprising instructions executable by a computer system (104) to cause said computer system (104)

a) to control temperature influencing means (107) connected to said computer system (104) to provoke an initial local temperature change in the proximity of a first place (101) of a patient's vascular system (103) (S4), thus introducing a travelling temperature deviation to patient's blood stream, b) to record said patient's local blood temperature measured by a temperature sensor device (117) at a second place (102) of patient's vascular system (103) downstream of said first place (101) as a function of time (S17) to determine a thermodilution curve (15), c) to determine an extravascular thermovolume (112) estimate from said thermodilution curve (15) (S23), d) to determine a new initial local temperature change depending on said thermovolume (112) estimate (S24), e) to control said temperature influencing means (107) to provoke said new initial local temperature change in the proximity of said first place (101)(S27), f) to determine an improved thermodilution curve (17), and g) to determine said cardio-vascular parameter from said improved thermodilution curve (17)(S43).

16. Computer program as claimed in claim 15, wherein said temperature influencing means (107) is an injection means (107) for injecting a liquid having a temperature different from the temperature of patient's blood, provoking said initial local temperature change is achieved by said injection means (107) injecting at said first place (101) a first amount of liquid into said vascular system (103)(S4), said liquid having a first temperature different from the temperature of patient's blood, and provoking said new temperature difference is achieved by said injection means (107) injecting at said first place (101) a second amount of liquid into said vascular system (103)(S27), said liquid having a second temperature different from the temperature of patient's blood.

17. Computer program as claimed in claim 16, wherein said second temperature is different from said first temperature.

18. Computer program as claimed in any of claims 16 or 17, wherein said second amount is different from said first amount.

19. Computer program as claimed in claim 15 wherein said cardio-vascular parameter is determined by transpulmonary thermodilution and said extravascular thermovolume (112) estimate correlates to an estimate of Extravascular Lung Water.

20. Computer program as claimed in claim 15 wherein said extravacular thermovolume (112) estimate is determined from a cardiac output derived from said thermodilution curve (15), a downslope of said thermodilution curve (15), and a mean transit time estimate derived from said thermodilution curve (15) indicating an estimate of the time required by said temperature deviation to travel from said first place (101) to said second place (102).

21. Computer program as claimed in claim 15 wherein said cardio-vascular parameter is the cardiac output.

* * * * *